(12) United States Patent
Day et al.

(10) Patent No.: US 8,383,632 B2
(45) Date of Patent: Feb. 26, 2013

(54) METHOD FOR MAKING CETIRIZINE TABLETS

(75) Inventors: Kenneth Day, Harleysville, PA (US); Kangping Xiao, Westfield, NJ (US); Satish Kamath, Mason, OH (US); Indu Shah, North Wales, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 372 days.

(21) Appl. No.: 12/553,157

(22) Filed: Sep. 3, 2009

(65) Prior Publication Data

US 2010/0062061 A1 Mar. 11, 2010

Related U.S. Application Data

(60) Provisional application No. 61/094,605, filed on Sep. 5, 2008.

(51) Int. Cl.
*A61K 31/496* (2006.01)
(52) U.S. Cl. ............... 514/255.04; 514/58; 544/396
(58) Field of Classification Search .......... 514/58, 514/255.04; 544/396
See application file for complete search history.

(56) References Cited

U.S. PATENT DOCUMENTS

| | | | |
|---|---|---|---|
| 3,185,626 A | 5/1965 | Baker | |
| 4,543,370 A | 9/1985 | Porter et al. | |
| 4,643,894 A | 2/1987 | Porter et al. | |
| 4,683,256 A | 7/1987 | Porter et al. | |
| 4,725,441 A | 2/1988 | Porter et al. | |
| 4,802,924 A | 2/1989 | Woznicki et al. | |
| 4,828,841 A | 5/1989 | Porter et al. | |
| 5,244,881 A | 9/1993 | Coutel-Egros | |
| 5,630,871 A | 5/1997 | Jordan | |
| 5,658,589 A | 8/1997 | Parekh et al. | |
| 6,245,353 B1 * | 6/2001 | Tritthart et al. | 424/466 |
| 6,274,162 B1 | 8/2001 | Steffenino et al. | |
| 6,455,533 B1 * | 9/2002 | Fanara et al. | 514/255.04 |
| 6,602,518 B2 * | 8/2003 | Seielstad et al. | 424/439 |
| 6,767,200 B2 | 7/2004 | Sowden et al. | |
| 2004/0156902 A1 | 8/2004 | Lee et al. | |
| 2005/0152970 A1 | 7/2005 | Rinker et al. | |

FOREIGN PATENT DOCUMENTS

| | | |
|---|---|---|
| EP | 0811374 A1 | 10/1997 |
| WO | WO 03/059328 A1 | 7/2003 |
| WO | WO 2007/025767 A | 3/2007 |
| WO | WO 2009/006898 A | 1/2009 |

OTHER PUBLICATIONS

PCT International Search Report for International Appl. No. PCT/US2009/055809 dated Nov. 18, 2009.
Orally Disintegrating Tablets, Guidance for Industry, Draft Guidance, Food and Drug Administration, Apr. 2007.

* cited by examiner

*Primary Examiner* — Ali Soroush
(74) *Attorney, Agent, or Firm* — William E. McGowan

(57) ABSTRACT

In one aspect, the present invention features a method of producing a tablet including cetirizine including the steps of: (i) mixing cetirizine, a polyol, and a solvent for the cetirizine to form a cetirizine:polyol complex, wherein the solvent comprises water and an alkalizing agent and has a pH from about 2 to about 7; (ii) isolating particles of the cetirizine:polyol complex from the mixture; and (iii) forming the particles into a tablet.

20 Claims, No Drawings

METHOD FOR MAKING CETIRIZINE TABLETS

CROSS REFERENCE TO RELATED APPLICATIONS

This application claims the benefit of priority from U.S. Provisional Patent Application No. 61/094,605, filed on Sep. 5, 2008, the content of which is incorporated by reference.

BACKGROUND OF THE INVENTION

Polyols, such as cyclodextrins, sugars, and other carbohydrates are used in tablets containing pharmaceutically active agents for various purposes, such as for taste-masking purposes in chewable tablets or for bulk filling purposes in fast dissolving tablets. The pharmaceutically active agent cetirizine, however, is both bitter and highly susceptible to degradation by esterification with polyols. PCT Patent Application WO 03/059328 discloses that esterification of cetirizine can be controlled by creating a very dry environment and/or by physical separation of cetirizine and polyols in the tablet. However, such a process fail to create an effective environment for taste-masking purposes, as the resulting tablet will have an initial taste of bitterness as the cetirizine must initially dissolve in the mouth prior to initiation of the "in-situ" taste-masking effect of the polyol in the tablet.

Applicants, however, have unexpectedly found a process by which that cetirizine and polyols can be physically combined for use in a tablet without causing a significant esterification to the cetirizine. Specifically, it has been unexpectedly found that the addition of an alkalizing agent coupled with a wet formulation process allows for the presence of cetirizine and polyols together in the same formulation, and further unexpectedly at levels higher than ten molar equivalents as is specified in PCT Patent Application WO 03/059328. By combining cetirizine and polyols in a wet formulation, it is now possible for cetirizine-polyol complexation to occur during the manufacturing process of the tablet, thereby eliminating the drawbacks of the above-discussed in-situ complexation.

SUMMARY OF THE INVENTION

In one aspect, the present invention features a method of producing a tablet including cetirizine including the steps of: (i) mixing cetirizine, a polyol, and a solvent for the cetirizine to form a cetirizine:polyol complex, wherein the solvent contains water and an alkalizing agent and has a pH from about 2 to about 7; (ii) isolating particles of the cetirizine:polyol complex from said mixture; and (iii) forming the particles into a tablet. In another aspect, the present invention features a tablet containing cetirizine that is manufactured by such method.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

Cetirizine

What is meant by cetirizine is the compound [2-[4-[(4-chlorophenyl)phenylmethyl]-1-piperazinyl]ethoxy]acetic acid, including isomers thereof (such as 2-[2-[4-[(R)-(4-chlorophenyl)-phenyl-methyl]piperazin-1-yl]ethoxy]acetic acid known as levocetirizine), and pharmaceutically acceptable salts thereof (such as cetirizine dihydrochloride and levocetirizine dihydrochloride).

In one embodiment, the particles contains from about 0.5 to about 20 percent by weight of cetirizine, such as from about 1 to about 10 percent by weight of cetirizine. In one embodiment, the tablet contains from about 0.5 mg to about 20 mg of cetirizine, such as from about 1 mg to about 10 mg of cetirizine.

Polyol

What is meant by a polyol is a compound comprising two or more hydroxyl groups. Examples of polyols include, but are not limited to, sugars alcohols such as mannitol, xylitol, sorbitol and erythritol; sugars such as sucrose, fructose, mannose, dextrose, lactose such as lactose monohydrate, and isomalt; cyclodextrins such as beta-cyclodextrin and alpha-cyclodextrin.

In one embodiment, the particles contain from about 25 to about 95 percent by weight of one or more polyols, such as from about 40 percent to about 90 percent by weight of one or more polyols, such as from about 45 percent to about 70 percent. In one embodiment, the tablet contains from about 50 percent to about 98 percent by weight of one or more polyols, such as from about 80 percent to about 95 percent by weight of one or more polyols.

Solvent

The process of invention involves dissolving the cetirizine in a solvent containing water. The solvent may also contain alcohols such as ethanol, methanol, and isopropanol, and mixtures thereof.

In one embodiment, the pH of the solvent is from about 2 to about 7, such as from about 2.4 to about 4. Applicants have found that increasing the pH too much can cause neutralization of the tertiary amine groups of cetirizine, making them susceptible to oxidation or other forms of degradation that may be inhibited by a protonated amine salt. Therefore, it is important that the pH (e.g., the amount of alkalizing agent used) is balanced in such a way as to inhibit esterification while also maintaining sufficient protonation of the tertiary amine functional groups such that their stability is not compromised. Furthermore, this approach stabilizes cetirizine against any nucleophilic addition to the carbonyl carbon, including but not limited to amidation reactions.

In one embodiment, an alkalizing agent is added to the solvent. Examples of alkalizing agents that can be used to increase the pH of the solvent include, but are not limited to, sodium bicarbonate and sodium citrate, sodium ascorbate, sodium or other salts of phosphate, sulfate, sulfonate, aluminum hydroxide, magnesium hydroxide carbonates of alkaline salts such as calcium carbonate, magnesium hydroxide, magnesium carbonate, aluminum magnesium hydroxide carbonate, trometamol, disodium succinate, sodium hydrogen phosphate, trisodium phosphate, dipotassium phosphate, and L-arginine.

In one embodiment, the amount of alkalizing agent is added to the cetirizine and polyol mixture is at a level sufficient to minimize ester degradation and oxidative degradation. Degradation is measured by the amount of degradation analyzed after storage of the tablet at accelerated conditions of 40° C. and 75% relative humidity as a function of the percentage of the initial amount of cetirizine for a period of 3 months. In one embodiment, the level of cetirizine:polyol ester degradant is less than 0.5 percent, and the largest cetirizine oxidative degradant is less than 0.5 percent, such as less than 0.2 percent. In one embodiment, the alkalizing agent is added in an amount from about 0.25 to about 1.5 molar equivalents of cetirizine, such as from about 0.5 to about 1 molar equivalents of cetirizine.

Manufacture of Particles Containing Cetirizine:Polyol Complex

The particles containing the cetirizine:polyol complex may be prepared and isolated (e.g., by removing the solvent by drying) in a variety of methods, including spray drying and wet granulation. Spray drying techniques involve mixing of the solvent with the cetirizine, the polyol and the alkalizing agent into a slurry or suspension wherein the slurry or suspension is sprayed and dried in a single step which results in a uniform granule or particle containing these materials.

Wet granulation involves various methods including low shear mixers (e.g., planetary mixers), high shear granulation, and fluid bed granulation. In these processes, the solvent is added to the polyol and cetirizine, and the combined complex is subsequently dried in a tray oven or a fluid bed processing unit. In one embodiment of high shear wet granulation, the alkalizing agent is added to the granulating liquid containing the solvent, and sprayed or distributed to the bed containing cetirizine and the polyol, and the mixture is subsequently dried. In another embodiment of high shear wet granulation, the alkalizing agent and cetirizine are added to the granulating liquid containing the solvent and subsequently distributed into the bed containing the polyol, following which the mixture subsequently dried. In another embodiment of high shear wet granulation the polyol, cetirizine and alkalizing agent are blended in the high shear granulator, the granulating liquid containing the solvent is distributed into the mixture, and the resulting mixture is subsequently dried. In yet another embodiment, a separate binder is added to the granulating liquid or to the bed in order to facilitate physical binding of the materials into a granulation. Suitable wet binders include, but are not limited to, hypromellose, polyvinyl pyrrolidone, pregelatinized starch, cooked starch, and hydroxypropyl cellulose.

In one embodiment of fluid bed granulation, the polyol and cetirizine are added to the bed, and the alkalizing agent is added to the granulating liquid containing the solvent and sprayed onto the bed, following which the resulting mixture is subsequently dried. In another embodiment of fluid bed granulation, the polyol and alkalizing agent are added to the bed, and the cetirizine is added to the granulating liquid containing the solvent and sprayed onto the bed, following which the resulting mixture is subsequently dried. In another embodiment of fluid bed granulation, the polyol, alkalizing agent, and cetirizine are added to the bed, and the granulating liquid containing the solvent and sprayed onto the bed, following which the resulting mixture is subsequently dried. In another embodiment of fluid bed granulation, the polyol is added to the bed, and the cetirizine and alkalizing agent are added to the granulating liquid containing the solvent and sprayed onto the bed, following which the resulting mixture is subsequently dried. In the cases of fluid bed granulation wherein the cetirizine is dissolved in the granulating liquid and sprayed onto the polyol substrate or polyol and alkalizing agent substrate, this process is also known herein as drug layering. In one embodiment, the polyol may also be combined with an inert substrate such as microcrystalline cellulose.

In one embodiment, the resulting granulated material may then be dried, and optionally dry-blended with further ingredients (e.g., excipients such as lubricants and colorants). The final dry blend is then suitable for compression. Methods for direct compression and wet granulation processes are known in the art. In one embodiment, the tablet matrix includes a wet granulation, which is formulated to have modified release properties. As used herein, the term matrix is defined as the portion of the tablet that does not contain the granulation or layered particle containing the cetirizine and polyol.

In one embodiment the complex containing cetirizine and a polyol also contains a second active ingredient. In one embodiment the second active ingredient is for the treatment of an upper respiratory disorder, such as a pharmaceutically active agent selected from the group of phenylephrine, loratadine, fexofenadine, diphenhydramine, dextromethorphan, chlorpheniramine, chlophedianol, and pseudoephedrine.

In one embodiment the second active ingredient in the cetirizine:polyol complex or in the matrix is an analgesic, anti-inflammatories, and antipyretics. Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Manufacture of Tablets

In one embodiment of the invention, the particles containing the cetirizine and a polyol are mixed with a tablet matrix. In one embodiment, the carrier has an average particle size of about 50 microns to about 500 microns, such as between 50 microns and 300 microns. Particles in this size range are particularly useful for direct compression processes.

In embodiment, the components of carrier and the particles are blended together, for example as dry powders, to form a tablet matrix and fed into the die cavity of an apparatus that applies pressure to form a tablet. Any suitable compacting apparatus may be used, including, but not limited to, conventional unitary or rotary tablet press. In one embodiment, the tablet may be formed by compaction using a rotary tablet press (e.g., such as those commercially available from Fette America Inc., Rockaway, N.J., or Manesty Machines LTD, Liverpool, UK). In general, a metered volume of the tablet matrix is filled into a die cavity, where the tablet matrix is either gravity fed or mechanically fed from a feeder, of the rotary tablet press, and the cavity rotates as part of a "die table" from the filling position to a compaction position. At the compaction position, the tablet matrix is compacted between an upper and a lower punch, then the resulting tablet is pushed from the die cavity by the lower punch and then guided to an injection chute by a stationary "take-off" bar. Advantageously, when utilized, a direct compression process may enable the minimization or elimination of water-soluble, non-saccharide polymeric binders such as polyvinyl pyrrolidone, alginates, hydroxypropyl cellulose, and hydroxypropylmethylcellulose, hydroxyethylcellulose, which could have a negative effect on dissolution.

In another embodiment, the tablet may be prepared by the compression methods and apparatus described in United States Patent Application Publication No. 20040156902. Specifically, the tablet may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional tablet matrix recovery system to recover excess tablet matrix from the filters and return the tablet matrix to the dies.

In one embodiment, the tablet is prepared by the compression methods and apparatus described in issued U.S. Pat. No. 6,767,200, the disclosure of which is incorporated herein by reference. Specifically, the tablet is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

In one embodiment of the invention, the tablet may be a directly compressed tablet made from a matrix that is substantially free of water-soluble polymeric binders and hydrated polymers. As used herein, what is meant by "substantially free" is less than 5 percent, such as less than 1 percent, such as less than 0.1 percent, such as completely free (e.g., 0 percent). This composition is advantageous for maintaining an immediate release dissolution profile, minimizing processing and material costs, and providing for optimal physical and chemical stability of the tablet. In one embodiment the density of the tablet is greater than about 0.9 g/cc.

The tablet may have one of a variety of different shapes. For example, the tablet may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet has one or more major faces. For example, the tablet surface typically has opposing upper and lower faces formed by contact with the upper and lower punch faces in the compression machine. In such embodiments the tablet surface typically further includes a "belly-band" located between the upper and lower faces, and formed by contact with the die walls in the compression machine. A tablet may also be a multilayer tablet. Alternatively, if tablets of the same composition are to be used in the dosage forms, the compression module may be equipped with multi-tip compression tooling. Four-tip tooling, for example, may be used to make four tablets within one die. The tablets may contain a single layer of multiple layers.

In one embodiment, the tablet matrix contains a second active ingredient. In one embodiment the second active ingredient is for the treatment of an upper respiratory disorder, wherein the pharmaceutically active agent is selected from the group of phenylephrine, loratadine, fexofenadine, diphenhydramine, dextromethorphan, chlorpheniramine, chlophedianol, and pseudoephedrine.

In certain embodiments, multilayer tablets can be produced with the invention described herein (e.g., bi-layer or tri-layer tablets can be produced). In one embodiment, the tablet die is filled with a first portion of the tablet matrix, the tablet matrix bed is optionally compressed a first time, a second portion of the tablet matrix is added, the tablet is compressed, and the tablet is ejected from the die. In one embodiment, the second portion of tablet matrix has the same blend composition as the first portion of tablet matrix. In another embodiment, the second portion of tablet matrix has a different composition from the first portion of tablet matrix. In one embodiment the first portion of the tablet matrix contains a pharmaceutically active agent (e.g., the cetirizine and polyol granulation of the present invention) and the second portion of the tablet matrix contains a different pharmaceutically active agent. In one embodiment, the first portion is for immediate release and the second portion is for modified release. In one embodiment the first portion contains an immediate release dose of the first and second pharmaceutically active agents, and the second portion contains a portion of the first pharmaceutically active agent coated with the coatings of the present invention and a modified release tablet matrix containing the second pharmaceutically active agent.

In another embodiment, the tablet is prepared as an orally disintegrating tablet. In such embodiments the cetirizine-polyol complex of the present invention is mixed with a carrier and formed into such a tablets. In one embodiment, the orally disintegrating tablet meets the criteria for Orally Disintegrating Tablets as defined by the draft Food and Drug Administration guidance, as published in April 2007, incorporated herein by reference. In one embodiment the orally disintegrating tablet meets a two-fold definition for orally disintegrating tablets including the following criteria: 1) that the tablet is one which contains medicinal substances and which disintegrates rapidly, usually within a matter of seconds, when placed upon the tongue and 2) be considered a solid oral preparation that disintegrates rapidly in the oral cavity, with an in-vitro disintegration time of approximately 30 seconds or less, when based on the United States Pharmacopeia (USP) disintegration test method for the specific medicinal substance or substances.

In embodiments where orally disintegrating tablets are prepared, the tablet matrix containing a carrier and the cetirizine:polyol complex are shaped in a preformed mold or blister. In one embodiment, the orally disintegrating tablets are prepared via a lyophilization process. Suitable carriers for a tablet prepared via a lyophilization process include, but are not limited to, lactose such as lactose monohydrate and dextrose such as dextrose monohydrate. Gums or viscosity modifying agents (such as xanthan gum, hypromellose, locust bean gum, sodium alginate, and carrageenan) may also be added to the matrix. Other materials such as binders, sweeteners, and acidulants may also be added to the matrix. In one embodiment of preparing such a tablet utilizing lyophilization, the cetirizine:polyol granule is mixed with the matrix carrier materials and a lyophilization solvent, introduced into a mold or blister, and freeze-dried and packaged or sealed.

Tablet Matrix

As discussed above, in one embodiment, the tablet is manufactured by mixing the particles with a tablet matrix. The carrier may contain one or more suitable excipients for the formulation of tablets. Examples of suitable excipients include, but are not limited to, fillers, adsorbents, binders, disintegrants, lubricants, glidants, release-modifying excipients, sweeteners, superdisintegrants, flavor and aroma agents, antioxidants, texture enhancers, and mixtures thereof.

Suitable fillers include, but are not limited to, water-soluble compressible carbohydrates such as sugars (e.g., dextrose, sucrose, maltose, and lactose), starches (e.g., corn starch), sugar-alcohols (e.g., mannitol, sorbitol, maltitol, erythritol, and xylitol), starch hydrolysates (e.g., dextrins, and maltodextrins), and water insoluble plastically deforming materials (e.g., microcrystalline cellulose or other cellulosic derivatives), and mixtures thereof. In one embodiment the precomplexed granule containing the polyol, cetirizine and alkalizing agent is blended with a suitable filler which does not contain cetirizine and is subsequently compressed in a matrix tablet. In one embodiment the matrix containing the filler is substantially free of an alkalizing agent. As used herein, substantially free is defined as less than about 0.5 percent, e.g. 0.1 percent by weight of the matrix. In one embodiment utilizing a multilayer tablet the second layer does not contain cetirizine and is substantially free of an alkalizing agent.

Suitable adsorbents (e.g., to adsorb the liquid drug composition) include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN™ brand (Fuji Chemical Industries (USA) Inc., Robbinsville, N.J.), clays, silicas, bentonite, zeolites, magnesium silicates, hydrotalcite, veegum, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Suitable release-modifying excipients include, but are not limited to, swellable erodible hydrophilic materials, insoluble edible materials, pH-dependent polymers, and mixtures thereof.

Suitable swellable erodible hydrophilic materials for use as release-modifying excipients include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly (ethylene oxide). Examples of suitable acrylic polymers include, but are not limited to, potassium methacrylatedivinylbenzene copolymer, polymethylmethacrylate, high-molecular weight cross-linked acrylic acid homopolymers and copolymers commercially available from Noveon Chemicals under the tradename CARBOPOL™ (e.g., having a viscosity of greater than 50,000 centipoise when tested using a Brookfield RVT Viscometer at 25° C., using spindle # 7, when dispersed in a basic solution). Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and tri-glycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof.

Suitable pH-dependent polymers for use as release-modifying excipients include, but are not limited to, enteric cellulose derivatives such as hydroxypropyl methylcellulose phthalate, hydroxypropyl methylcellulose acetate succinate, cellulose acetate phthalate; natural resins such as shellac and zein; enteric acetate derivatives such as polyvinylacetate phthalate, cellulose acetate phthalate, acetaldehyde dimethylcellulose acetate; and enteric acrylate derivatives such as polymethacrylate-based polymers such as poly(methacrylic acid, methyl methacrylate) 1:2 (which is commercially under the tradename EUDRAGIT S™), and poly(methacrylic acid, methyl methacrylate) 1:1 (which is commercially available under the tradename EUDRAGIT L™), and mixtures thereof.

Examples of suitable sweeteners include, but are not limited to, synthetic or natural sugars and high intensity sweeteners such as sucralose, saccharin, sodium saccharin, aspartame, acesulfame K or acesulfame, potassium acesulfame, thaumatin, glycyrrhizin, dihydrochalcone, alitame, miraculin, monellin, and stevside, and mixtures thereof. In one embodiment a high intensity sweetener is added to the precomplexed granulation containing cetirizine, a polyol and the alkalizing agent. In one embodiment a high intensity sweetener is added to the tablet matrix.

Examples of superdisintegrants include, but are not limited to, croscarmellose sodium, sodium starch glycolate and cross-linked povidone (crospovidone). In one embodiment the tablet contains up to about 5 percent by weight of such superdisintegrant.

Examples of suitable flavor and aroma agents include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry, and black currant); artificial and natural flavors of brews and liquors (e.g., cognac, whisky, rum, gin, sherry, port, and wine); tobacco, coffee, tea, cocoa, and mint; fruit juices including expelled juice from washed, scrubbed fruits such as lemon, orange, and lime; mint; ginger; cinnamon; cacoe/cocoa; vanilla; liquorice; menthol; eucalyptus; aniseeds nuts (e.g., peanuts, coconuts, hazelnuts, chestnuts, walnuts, and colanuts); almonds; raisins; and powder, flour, or vegetable material parts including tobacco plant parts (e.g., the genus Nicotiana in amounts not contributing significantly to a level of therapeutic nicotine), and mixtures thereof.

Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1 percent to about 10 percent by weight.

In one embodiment, the tablet matrix is substantially free of an alkalizing agent.

Tablets Coatings

In one embodiment, the method of the present invention furthers includes coating the tablet (e.g., with an outer coating). In one embodiment, the method further includes coating the tablet with a subcoating prior to applying the outercoating to the tablet.

Subcoating

In one embodiment, tablet contains one or more subcoating layers. In one embodiment, the subcoating layer substantially covers the surface of the tablet. The use of subcoatings is well known in the art and disclosed in, for example, U.S. Pat. No. 3,185,626, which is incorporated by reference herein. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Suitable subcoatings may include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates; pigments; and opacifiers.

In embodiment, the subcoating includes, based upon the total weight of the subcoating, from about 2 percent to about 8 percent (such as from about 4 percent to about 6 percent of a water-soluble cellulose ether and from about 0.1 percent to about 1 percent castor oil), as disclosed in detail in U.S. Pat. No. 5,658,589, which is incorporated by reference herein. In another embodiment, the subcoating includes, based upon the total weight of the subcoating, from about 20 percent to about 50 percent (such as from about 25 percent to about 40 percent) of HPMC; from about 45 percent to about 75 percent (such as from about 50 percent to about 70 percent) of maltodextrin; and from about 1 percent to about 10 percent (such as from about 5 percent to about 10 percent) of PEG 400.

The subcoating typically is present in an amount, based upon the dry weight of the tablet, from about 0 percent to about 5 percent. The dried dip coating layer typically is present in an amount, based upon the dry weight of the tablet and the optional subcoating, from about 1.5 percent to about 10 percent. In one embodiment the tablet is substantially free of a subcoating.

Outer-Coating

What is meant by outer-coating is the coating on the outer surface of the coated tablet. In one embodiment, the outer-coating substantially covers (e.g., covers at least 90 percent) the surface of the tablet.

The average thickness of the dried dip-coating layer typically is from about 40 to about 400 microns. However, one skilled in the art would readily appreciate without undue experimentation that the dip coating thickness may be varied in order to provide a smoother, easier to swallow, tablet or to achieve a desired dissolution profile. Moreover, the thickness of dipped film coatings may vary at different locations on the substrate depending upon its shape. For example, the thickness of the coating at an edge or corner of a substrate may be as much as 50 percent to 70 percent less than the thickness of the coating at the center of a major face of the substrate. This difference can be minimized by, for example, use of a thicker subcoating, or use of dipping compositions that result in higher weight gains on the substrate.

In embodiments wherein a thicker dip coating is desired, an effective amount of a weight gain enhancer (e.g., simethicone, polysorbate 80 and mixtures thereof) may be added to a film forming composition containing a film former and an optional thickener such as a hydrocolloid. The weight gain enhancer is used in an amount sufficient to increase the weight gain of the coating liquid, e.g. by at least about 10 percent, by at least about 20 percent, or by at least about 30 percent on a substrate when dried. The percent weight gain increase is determined based upon the difference between the total weight of the coated substrate with the coating composition including the weight gain enhancer, and the total weight of an coated equivalent substrate, which has been coated under similar processing conditions with a coating composition that does not include an effective amount of weight gain enhancer.

In one embodiment, the method further includes creating one or more openings in the subcoating in the portion of the tablet that is not coated with the outer-coating, to expose the tablet on the surface of the coated tablet, such as described in US Patent Application No. 2005/0152970.

In one embodiment, the method further includes creating one or more openings in the outer-coating to expose the tablet, not through the subcoating, as disclosed in US Patent Application No. 2005/0152970. Since gelatin is not compatible with laser drilling, it is necessary in tablets with such gelatin coating, to expose the subcoat before laser drilling the openings.

In one embodiment the outer-coating covers only a portion of the tablet such as only one half of the coated tablet. The other half of the tablet may contain a separate type of the outer-coating such as gelatin, or expose only the subcoat or tablet.

In certain embodiments in which modified release of the pharmaceutically active agent is desired, the pharmaceutically active agent or the tablet may optionally be coated with a known release-modifying coating. This advantageously provides an additional tool (e.g., in addition to the modified release coating on the particles) for modifying the release profile of pharmaceutically active agent from the tablet. In one embodiment, the coating contains a film-forming pH-dependent polymer, such as enteric polymers. In one embodiment, the outer coating is a modified release coating and the active particles in the tablet have a different modified release, so that variable release rates can be demonstrated; including a pulsatile release demonstrated by the tablet coating and a first order release demonstrated by the coated pharmaceutically active agent. In another embodiment, the outer modified release coating is placed on the tablet to release the a second uncoated pharmaceutically active agent particle from the tablet in a modified release manner, and the first particle coated pharmaceutically active agent in a separate modified release manner.

As used herein, "substantially coated" shall mean that less than about 20 percent, e.g. less than about 15 percent, or less than about 1.0 percent of the surface area of a tablet is exposed, e.g. not covered, with a desired coating.

In one embodiment, the tablet coating contains a thermoplastic film-forming water soluble polymer, such as a hydroxypropylmethylcellulose compound. An example of such a compound is "HPMC 291", which is a cellulose ether having a degree of substitution of about 1.9 and a hydroxypropyl molar substitution of 0.23, and containing, based upon the total weight of the compound, from about 29 percent to about 30 percent methoxyl groups and from about 7 percent to about 12 percent hydroxylpropyl groups. HPMC 2910 is commercially available from the Dow Chemical Company under the tradename METHOCEL E™. METHOCEL ES™, which is one grade of HPMC-2910 suitable for use in the present invention, has a viscosity of about 4 to 6 cps (4 to 6 milipascal-seconds) at 20 C in a 2 percent aqueous solution as determined by a Ubbelohde viscometer. Similarly, METHOCEL E6™, which is another grade of HPMC-2910 suitable for use in the present invention, has a viscosity of about 5 to 7 cps (5 to 7 milipascal-seconds) at 20 C in a 2 percent aqueous solution as determined by a Ubbelohde viscometer. METHOCEL E15™, which is another grade of HPMC-2910 suitable for use in the present invention, has a viscosity of about 15000 cps (15 milipascal-seconds) at 20 C in a 2 percent aqueous solution as determined by a Ubbelohde viscometer. As used herein, "degree of substitution" means the average number of substituent groups attached to an anhydroglucose ring, and "hydroxypropyl molar substitution" means the number of moles of hydroxypropyl per mole anhydroglucose.

In one embodiment, the coating contains a polyvinyl alcohol and polyethylene glycol copolymer. One suitable polyvinyl alcohol and polyethylene glycol copolymer for use as a tablet coating is commercially available from BASF Corporation under the tradename KOLLICOAT IR™.

In one embodiment, the coating contains a modified starch. As used herein, "modified starches" for use in the tablet coating include starches that have been modified by crosslinking, chemically modified for improved stability or optimized performance, or physically modified for improved solubility properties or optimized performance. Examples of chemically-modified starches are well known in the art and typically include those starches that have been chemically treated to cause replacement of some of its hydroxyl groups with either ester or ether groups. Crosslinking, as used herein, may occur in modified starches when two hydroxyl groups on neighboring starch molecules are chemically linked. As used herein, "pre-gelatinized starches" or "instantized starches" refers to modified starches that have been pre-wetted, then dried to enhance their cold-water solubility.

Suitable modified starches for use in the tablet coating are commercially available from several suppliers such as, for example, A. E. Staley Manufacturing Company, and National Starch & Chemical Company. One suitable film forming modified starch includes the pre-gelatinized waxy maize derivative starches that are commercially available from National Starch & Chemical Company under the tradenames PURITY GUM™ and FILMSET™, and mixtures thereof. Such waxy maize starches typically contain, based upon the total weight of the starch, from about 0 percent to about 18 percent of amylose and from about 100 percent to about 88 percent of amylopectin.

Other suitable film forming modified starches for use in the tablet coating include the hydroxypropylated starches, in which some of the hydroxyl groups of the starch have been etherified with hydroxypropyl groups, usually via treatment with propylene oxide. One example of a suitable hydroxypropyl starch that possesses film-forming properties is available from Grain Processing Company under the tradename, PURE-COTE B790™

In one embodiment, the tablet coating contains a tapioca dextrin. Suitable tapioca dextrins for use as film formers as tablet coatings include, but are not limited to, those available from National Starch & Chemical Company under the tradenames CRYSTAL GUM™ or K-4484™, and derivatives thereof such as modified food starch derived from tapioca, which is available from National Starch and Chemical under the tradename PURITY GUM 40™, and copolymers and mixtures thereof.

In one embodiment, the tablet coating contains a thickener. Examples of such thickeners include but are not limited to hydrocolloids (also referred to herein as gelling polymers), clays, gelling starches, and crystallizable carbohydrates, and mixtures thereof.

Examples of suitable hydrocolloids (also referred to herein as gelling polymers) for use as a tablet coating include alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and mixtures thereof. Examples of suitable gelling starches include acid hydrolyzed starches, and mixtures thereof. Additional suitable thickening hydrocolloids include low-moisture polymer solutions such as mixtures of gelatin and other hydrocolloids at water contents up to about 30 percent, such as for example those used to make "gummi" confection forms. Additional suitable thickeners include, but are not limited to, crystallizable carbohydrates.

In one embodiment of the invention, the tablet coating contains gelatin. Gelatin is a natural, thermogelling polymer. It is a tasteless and colorless mixture of derived proteins of the albuminous class, which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67 percent gelatin gel that has been held at 10 C for 17 hours. In a preferred embodiment, the flowable material is an aqueous solution including 20 percent 275 Bloom pork skin gelatin, 20 percent 250 Bloom Bone Gelatin, and approximately 60 percent water.

Use of Tablet

In one embodiment, the present invention features a method of treating an ailment, the method including orally administering the above-described tablet wherein the tablet includes an amount of cetirizine effective to treat the ailment. Examples of such ailments include, but are not limited to, In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

EXAMPLES

Specific embodiments of the present invention are illustrated by way of the following examples. This invention is not confined to the specific limitations set forth in these examples.

Example 1

Fluid Bed Granulation Containing Cetirizine

Part A: Preparation of Granulating Solution Containing Cetirizine

A granulating solution of 10% polyvinylpyrrolidone (PVP) is prepared by adding 5400 g of purified water at 25° C. to a suitable vessel. A laboratory rotary mixer is added to the water and 600 g of PVP is added while mixing at 100 RPM. The mixing speed is then lowered to 50 RPM and allowed to mix for approximately 30 minutes.

Part B: Preparation of Cetirizine Granulation

As indicated in Table 1, Cetirizine Dihydrochloride, Beta-cyclodextrin, Sodium Succinate, and Corn Starch are charged into a Fluid Bed Granulator. Approximately 3000 g of Purified Water is then sprayed into the bed at approximately 75-125 g/minute and an inlet air temperature of approximately 55° C., using an atomization air pressure of 2 bar. Approximately 5680 g of the solution prepared in Step A is then sprayed onto the granulation at approximately 75 to 125 g/minute, using an inlet air temperature of approximately 55° C., using an atomization air pressure of 2 bar. Following spraying, the granulation is dried to a product temperature endpoint of approximately 30° C., or a Loss on Drying Analysis (LOD) of approximately 7.5%.

TABLE 1

Cetirizine Granulation Formulation

| Material | g/batch |
| --- | --- |
| Cetirizine Dihydrochloride | 1000 |
| Beta-Cyclodextrin (12.5% moisture) | 8428 |
| Sodium Succinate (anhydrous) | 175.5 |

TABLE 1-continued

Cetirizine Granulation Formulation

| Material | g/batch |
| --- | --- |
| Corn Starch | 4214 |
| PVP | 568 |
| TOTAL | 14385.5 |

Example 2

Preparation of Spray Drying Solution Containing Cetirizine

Part A: Preparation of Spray Drying Slurry

A slurry of the materials presented in Table 2 is prepared by charging a suitable stainless steel vessel with 3000 g of water. While mixing using a laboratory mixer at 50 RPM, the Cetirizine Dihydrochloride and Sodium Succinate are dissolved into the water. The Beta-Cyclodextrin is then added to the mixture and dispersed while mixing to form the slurry.

TABLE 2

Spray Drying Slurry formulation for Spray Drying

| Material | g/batch |
| --- | --- |
| Cetirizine Dihydrochloride | 1000 |
| Sodium Succinate (anhydrous) | 175.4 |
| Water | 3000 |
| Beta-cyclodextrin | 4214 |

Part B: Spray Drying Process

The slurry from part A is pumped and spray dried in a laboratory spray drier commercially available from Niro Systems (model PSD-1) at spray rate of approximately 100 g/minute and an atomization pressure of approximately 1.0 bar, and an outlet gas temperature of 90° C. The resulting particles are then collected.

Example 3

High Shear Granulation Process Using Cetirizine

A 65 L TK Fielder high sheer granulator equipped with a chopper is used for high shear granulation. The Cetirizine Dihydrochloride, Beta-cyclodextrin, PVP and Sodium Succinate are charged into the granulator and mixed for approximately 1 minute while with the chopper active. 1000 g of purified water is slowly added over 2 minutes while mixing and with the chopper active. The Corn Starch is then added and allowed to mix for 1 minute. The granulation is then dried in a Glatt GCPG 15 kg drying unit to a final LOD of approximately 7%.

TABLE 3

High Shear Granulation Containing Cetirizine Blend

| Material | g/batch |
| --- | --- |
| Cetirizine HCl | 1000 |
| Beta-Cyclodextrin (12.5% moisture) | 8428 |
| Sodium Succinate (anhydrous) | 175.5 |
| Corn Starch | 4214 |
| PVP | 568 |
| TOTAL | 14385.5 |

Example 4

Single Layer Compressed Chewable Tablets Containing Cetirizine

Part A: Chewable Tablet Formulation & Blending

The granulated or spray dried particles from Examples 1, 2, and 3 are separately utilized to produce three different chewable tablet blends using the formulation outlined in Table 4. The Crospovidone, Sucralose, Succinic Acid, Flavors, Dye, and Lake are screened manually through a 60 mesh screen to form a flavor blend. The Mannitol is manually screened through a 14 mesh screen. Approximately one half of the Mannitol and the entire flavor blend are added to a suitable v-blender. The remainder of the mannitol is added to the v-blended and blended end-over-end for approximately 7 minutes. The Magnesium Stearate and Stearic Acid are screened manually through a 60 mesh screen and added to the v-blender. The blend is blended end-over-end in the v-blender for 2 minutes. The 3 blends are individually discharged into 3 different plastic bags.

TABLE 4

Chewable Tablet Formulation

| Material | Amount (g) |
| --- | --- |
| Particles from Examples 1, 2, or 3 | 14386 |
| Mannitol | 29617 |
| Crospovidone | 500 |
| Sucralose | 175 |
| Grape Flavor | 180 |
| Succinic Acid | 90 |
| Sweet Flavor | 45 |
| Carmine Coloring | 54 |
| Blue Coloring | 54 |
| Stearic Acid | 450 |
| Magnesium Stearate | 225 |
| TOTAL | 45000 |

Part B: Compression Procedure

The resulting dry blends from Part A of this Example are compressed into tablets on a rotary tablet compression module as described in col. 12, lines 14-20 of U.S. Pat. No. 6,767,200 using 7/16 inch extra deep concave tablet tooling. The compression module is a double row, rotary apparatus, comprising a fill zone, insertion zone, compression zone, ejection zone, and purge zone as shown in FIG. 6 of U.S. Pat. No. 6,767,200. The dies of the compression module are filled using vacuum assistance, with mesh screen filters located in die wall ports of each die. The resulting tablets have an average weight of 450 mg, a thickness of 0.306 inches, and a hardness of 3.2 kp.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

The compressed tablets utilizing the prepared cetirizine-polyol complex samples from Examples 1, 2 and 3 were analyzed for cetirizine stability at accelerated conditions. The data for cetirizine degradation is shown in Table 6 and Table 8.

Example 5

High Shear Granulations in Hobart Mixer Using Beta-Cyclodextrin

The dry materials outlined in Table 5 below (except for the cetirizine, sodium citrate, sodium succinate, and corn starch) were first combined in a Hobart mixer at a low speed. In samples B, the sodium citrate, and in sample C, the sodium succinate, were also added to the dry ingredients. Cetirizine dihydrochloride was then mixed into an aqueous solution at 9.09% solids weight/weight using purified water. In samples D and E, the sodium succinate was added to this solution.

The solution was then sprayed into the dry materials while mixing over about 15 minutes. The corn starch was then added over 2 minutes with continued mixing. The granulation was tray dried at 50° C. for about 2 hours. The granulation was then added back into the mixer and croscarmellose sodium was added and mixed for about 2 minutes. The magnesium stearate and stearic acid were then added and mixed for an additional 1 minute.

TABLE 5

High Shear Granulations Formulation

| Material (weight) | Sample A | Sample B | Sample C | Sample D | Sample E |
| --- | --- | --- | --- | --- | --- |
| Cetirizine HCl | 5.00 g | 5.00 g | 5.00 g | 5.00 g | 5.00 g |
| Beta-cyclodextrin | 42.14 g | 42.14 g | 42.14 g | 42.14 g | 42.14 g |
| Sodium Succinate | 0.00 g | 0.00 g | 4.39 g | 4.39 g | 0.73 g |
| Sodium Citrate | 0.00 g | 12.75 g | 0.00 g | 0.00 g | 0.00 g |
| Polyvinylpyrrolidone (Kollidon 30-LP ™) | 5.00 g | 5.00 g | 5.00 g | 5.00 g | 5.00 g |
| Avicel pH102 (Microcrystalline cellulose) | 119.10 g | 107.90 g | 116.40 g | 116.40 g | 118.60 g |
| Corn Starch | 20.00 g | 20.00 g | 20.00 g | 20.00 g | 20.00 g |
| Croscarmellose Sodium | 5.00 g | 5.00 g | 5.00 g | 5.00 g | 5.00 g |
| Magnesium Stearate | 1.30 g | 1.30 g | 1.30 g | 1.30 g | 1.30 g |
| Stearic Acid | 2.50 g | 2.50 g | 2.50 g | 2.50 g | 2.50 g |

These samples were then placed into a closed high density polyethylene bottle and analyzed for degradation in the form of the Beta-cyclodextrin ester and the oxidative degradant at 1 month, 40° C. and 75% relative humidity. The results, as shown in Table 6, show that between 0.25 and 5 molar equivalents of salt in relation to cetirizine, the level of ester is between 0.36% and "None Detected". When no salt is added, the ester level is present at 0.60%.

TABLE 6

| | Degradation | | | | |
|---|---|---|---|---|---|
| | Sample A | Sample B | Sample C | Sample D | Sample E |
| Sample Type | No Salt added | Salt as Solid | Salt as Solid | Salt in Solution | Salt in Solution |
| % Molar Eq. Salt | 0.00 | 5.00 | 1.50 | 1.50 | 0.25 |
| % Beta-cyclodextrin Ester | 0.60 | ND | ND | ND | 0.36 |
| % Oxidative Degradant | 0.02 | 0.04 | 0.05 | 0.04 | 0.02 |

ND—None Detected

Example 6

High Shear Granulations in Hobart Mixer Using Lactose

The dry materials outlined in Table 7 below (except for the cetirizine, sodium citrate, sodium succinate, and corn starch) were first combined in a Hobart mixer at a low speed. In samples B, the sodium citrate, and in sample C, the sodium succinate, were also added to the dry ingredients. Cetirizine dihydrochloride was then mixed into an aqueous solution at 9.09% solids weight/weight using purified water. In samples D and E, the sodium succinate was added to this solution.

The solution was then sprayed into the dry materials while mixing over about 15 minutes. The corn starch was then added over 2 minutes with continued mixing. The granulation was tray dried at 50° C. for about 2 hours. The granulation was then added back into the mixer and croscarmellose sodium was added and mixed for about 2 minutes. The magnesium stearate and stearic acid were then added and mixed for an additional 1 minute.

TABLE 7

| High Shear Granulations Formulation | | | | | |
|---|---|---|---|---|---|
| Material (weight) | Sample A | Sample B | Sample C | Sample D | Sample E |
| Cetirizine Dihydrochloride | 5.00 g | 5.00 g | 5.00 g | 5.00 g | 5.00 g |
| Lactose Monohydrate | 41.05 g | 41.05 g | 41.05 g | 41.05 g | 41.05 g |
| Sodium Succinate | 0.00 g | 0.00 g | 4.39 g | 4.39 g | 0.73 g |
| Sodium Citrate | 0.00 g | 12.75 g | 0.00 g | 0.00 g | 0.00 g |
| Polyvinylpyrrolidone (Kollidon 30-LP) | 5.00 g | 5.00 g | 5.00 g | 5.00 g | 5.00 g |
| Avicel pH102 (Microcrystalline cellulose) | 120.10 g | 108.90 g | 117.50 g | 117.50 g | 119.70 g |
| Corn Starch | 20.00 g | 20.00 g | 20.00 g | 20.00 g | 20.00 g |
| Croscarmellose Sodium | 5.00 g | 5.00 g | 5.00 g | 5.00 g | 5.00 g |
| Magnesium Stearate | 1.30 g | 1.30 g | 1.30 g | 1.30 g | 1.30 g |
| Stearic Acid | 2.50 g | 2.50 g | 2.50 g | 2.50 g | 2.50 g |

These samples were placed into a closed high-density polyethylene bottle and analyzed for Lactose ester and the oxidative degradant at 1 month, 40° C. and 75% relative humidity. The results show that between 0.25 and 5 molar equivalents of salt to cetirizine, the level of ester is between 0.32% and 0.06%. When no salt is added, the ester level is present at 0.63%. When the sodium citrate is added at 5 molar equivalents, the oxidative degradant is present at 0.24 percent. When the sodium succinate is present at 0.25 and 1.5 molar equivalents, the oxidative degradant is present at between 0.04 and 0.09 percent.

TABLE 8

| | Degradation | | | | |
|---|---|---|---|---|---|
| | Sample A | Sample B | Sample C | Sample D | Sample E |
| Sample Type | No Salt added | Salt as Solid | Salt as Solid | Salt in Solution | Salt in Solution |
| % Molar Eq. Salt | 0.00 | 5.00 | 1.50 | 1.50 | 0.25 |
| % Lactose Ester | 0.63 | 0.06 | 0.10 | 0.08 | 0.32 |
| % Oxidative Degradant | 0.02 | 0.24 | 0.09 | 0.09 | 0.04 |

The invention claimed is:

1. A method of producing a tablet comprising cetirizine, said method comprising the steps of:
   (i) mixing cetirizine, a polyol, an alkalizing agent and a solvent for said cetirizine to form a cetirizine:polyol complex, wherein said solvent comprises water and said mixture has a pH from about 2.5 to about 4;
   (ii) isolating particles of said cetirizine:polyol complex from said mixture; and
   (iii) forming said particles into a tablet; wherein said polyol is a cyclodextrin.

2. A method of claim 1, wherein said polyol is beta-cyclodextrin.

3. A method of claim 1, wherein said alkalizing agent is selected from the group consisting of sodium bicarbonate and sodium citrate.

4. A method of claim 1, wherein said cetirizine is cetirizine dihydrochloride.

5. A method of claim 1, wherein said cetirizine is levocetirizine dihydrochloride.

6. A method of claim 1, wherein said polyol and cetirizine are mixed together prior to being mixed with said solvent.

7. A method of claim 1, wherein said polyol, cetirizine, and alkalizing agent are mixed together prior to being mixed with said solvent.

8. A method of claim 1, wherein said polyol, cetirizine, and solvent are mixed via a fluidized bed process.

9. A method of claim 1, wherein said polyol, cetirizine, and solvent are mixed via a high-shear granulation process.

10. A method of claim 1, wherein said polyol, cetirizine, and solvent are mixed via a spray drying process.

11. A method of claim 1, wherein said method further comprising the step of blending said particles with a tablet matrix prior to forming said tablet.

12. A method of claim 11, wherein said tablet matrix comprises a polyol.

13. A method of claim 12, wherein said polyol comprised within said tablet matrix is selected from the group consisting of mannitol, sucrose, sorbitol, xylitol, erythritol, and dextrose.

14. A method of claim 1, wherein said tablet is orally disintegrating tablet matrix.

15. A method of claim 1, wherein said tablet is formed by compressing said particles.

16. A method of claim 1, wherein said tablet is formed by a lyophilizing said particles.

17. A method of claim 2, wherein said polyol, cetirizine, and alkalizing agent are mixed together prior to being mixed with said solvent.

18. A method of claim 2, wherein said alkalizing agent is selected from the group consisting of sodium bicarbonate and sodium citrate.

19. A method of claim 17, wherein said alkalizing agent is selected from the group consisting of sodium bicarbonate and sodium citrate.

20. A method of claim 19, wherein said cetirizine is cetirizine dihydrochloride.

* * * * *